US009105092B2

(12) United States Patent
Lee et al.

(10) Patent No.: US 9,105,092 B2
(45) Date of Patent: Aug. 11, 2015

(54) REGISTRATION METHOD OF IMAGES FOR SURGERY

(71) Applicant: KOH YOUNG TECHNOLOGY INC., Geumcheon-gu (KR)

(72) Inventors: Hyun-Ki Lee, Daegu (KR); Hae-Yong Yang, Anyang-si (KR); Young-Sik Kwon, Ansan-si (KR); Nozomu Matsumoto, Fukuoka (JP)

(73) Assignee: KOH YOUNG TECHNOLOGY INC., Seoul (KR)

( * ) Notice: Subject to any disclaimer, the term of this patent is extended or adjusted under 35 U.S.C. 154(b) by 0 days.

(21) Appl. No.: 14/001,793

(22) PCT Filed: Oct. 26, 2012

(86) PCT No.: PCT/KR2012/008848
§ 371 (c)(1),
(2) Date: Aug. 27, 2013

(87) PCT Pub. No.: WO2013/062348
PCT Pub. Date: May 2, 2013

(65) Prior Publication Data
US 2014/0226886 A1    Aug. 14, 2014

(30) Foreign Application Priority Data
Oct. 26, 2011    (KR) .................. 10-2011-0110189

(51) Int. Cl.
*G06T 3/00* (2006.01)
*A61B 5/00* (2006.01)
(Continued)

(52) U.S. Cl.
CPC ............ *G06T 3/0068* (2013.01); *A61B 5/0037* (2013.01); *A61B 5/055* (2013.01);
(Continued)

(58) Field of Classification Search
CPC ............... G06T 3/0068; G06T 7/003; G06T 2207/10081; A61B 5/0037; A61B 6/032
USPC ................... 382/131; 600/407, 411, 424
See application file for complete search history.

(56) References Cited

U.S. PATENT DOCUMENTS 6,560,354 B1 * 5/2003 Maurer et al. ................ 382/131
7,072,707 B2 * 7/2006 Galloway et al. ............. 600/424
(Continued)

FOREIGN PATENT DOCUMENTS

JP    2003-88508    3/2003
JP    2008-264520    11/2008
(Continued)

OTHER PUBLICATIONS

Written Opinion of the International Searching Authority for International Application No. PCT/KR2012/008848, dated Feb. 28, 2013.
(Continued)

*Primary Examiner* — Gregory M Desire
(74) *Attorney, Agent, or Firm* — Kile Park Reed & Houtteman PLLC

(57) ABSTRACT

In order for registration of images for surgery, first, a three-dimensional reference image of a surgical area of a patient before surgery is acquired. Then, a grating-pattern light is provided towards the surgical area to acquire a first measurement image. Thereafter, a preliminary registration is performed between the acquired first measurement image and a pre-acquired three-dimensional reference image. Then, a grating-pattern light is provided towards the surgical area after cutting out the surgical area to acquire a second measurement image. Thereafter, a fine registration is performed between the acquired second measurement image and the pre-acquired three-dimensional reference image based on the preliminary registration result. Thus, an accurate registration result may be acquired at low cost in a short period of time.

6 Claims, 7 Drawing Sheets

(51) Int. Cl.
  *A61B 5/055*  (2006.01)
  *A61B 6/03*  (2006.01)
  *G06T 7/00*  (2006.01)

(52) U.S. Cl.
  CPC ............... *A61B 6/032* (2013.01); *G06T 7/003* (2013.01); *G06T 7/0012* (2013.01); *G06T 2207/10081* (2013.01); *G06T 2207/10088* (2013.01); *G06T 2207/30008* (2013.01)

(56) References Cited

U.S. PATENT DOCUMENTS

| | | | |
|---|---|---|---|
| 7,693,256 B2* | 4/2010 | Brahme et al. | 378/41 |
| 8,126,241 B2* | 2/2012 | Zarkh et al. | 382/131 |
| 8,208,701 B2* | 6/2012 | Lendl | 382/128 |
| 8,295,577 B2* | 10/2012 | Zarkh et al. | 382/132 |
| 8,301,226 B2* | 10/2012 | Csavoy et al. | 600/424 |
| 2001/0035871 A1* | 11/2001 | Bieger et al. | 345/630 |
| 2009/0089034 A1* | 4/2009 | Penney et al. | 703/11 |
| 2010/0280365 A1* | 11/2010 | Higgins et al. | 600/424 |
| 2013/0317344 A1* | 11/2013 | Borus et al. | 600/411 |
| 2014/0226886 A1* | 8/2014 | Lee et al. | 382/131 |

FOREIGN PATENT DOCUMENTS

| | | |
|---|---|---|
| JP | 2010-237210 | 10/2010 |
| JP | 2010-243508 | 10/2010 |
| KR | 10-2007-0004074 | 1/2007 |
| KR | 10-2008-0032612 | 4/2008 |
| KR | 10-0961661 | 6/2010 |

OTHER PUBLICATIONS

International Search Report for International Application No. PCT/KR2012/008848 dated Feb. 28, 2013.

* cited by examiner

REGISTRATION METHOD OF IMAGES FOR SURGERY

TECHNICAL FIELD

The present invention relates to a registration method of images for surgery, and more particularly to a registration method of images for surgery capable of acquiring an accurate registration results at low cost in a short period of time.

BACKGROUND ART

Recently, a pre-taken image is widely used in surgery that treats affected part of a patient. Especially, in cases such as otorhinolaryngology surgery, the surgery should be carried out by avoiding nerves and organs of a patient, so the pre-taken image is required to carry out a highly accurate surgery.

In general, a pre-taken image includes a three-dimensional images such as an MRI image, a CT image, etc., and to perform an accurate registration between the pre-taken three-dimensional images and a real time three-dimensional images, various registration methods such as a method installing a marker on a surface of skin, a method using a template, a surface template-assisted marker position (STAMP) method, etc. have been studied.

However, the above mentioned conventional methods may have various problems such as an error according to a skin change that is incurred by installing a marker to the skin, a troublesome of producing a STAMP before surgery and a high cost for the production thereof, a lot of time is required for a registration, etc.

Therefore, compared to the prior arts, a registration method that may acquire accurate result at low cost in a short period of time is requested.

DETAILED DESCRIPTION OF THE INVENTION

Objects of the Invention

Therefore, the object of the invention is to provide a registration method of images for surgery capable of acquiring accurate registration results at low cost in a short period of time.

Technical Solution

In an exemplary embodiment of the present invention, a registration method of images for surgery includes acquiring a three-dimensional reference image of a surgical area of a patient before surgery. Then, a grating-pattern light is provided towards the surgical area. Thereafter, a first reflection image of the surgical area is acquired by the grating-pattern light. Then, a bucket algorithm is applied to the acquired first reflection image of the surgical area to measure a three-dimensional shape, and acquiring a first measurement image from the three-dimensional shape. Thereafter, a preliminary registration between the acquired first measurement image and the pre-acquired three-dimensional reference image is performed. Then, a grating-pattern light is provided towards a bone corresponding to the surgical area, after an incision of the surgical area. Thereafter, a second reflection image of the bone corresponding to the surgical area is acquired by the grating-pattern light. Then, a bucket algorithm is applied to the acquired second reflection image of the bone corresponding to the surgical area to measure a three-dimensional shape, and acquiring a second measurement image from the three-dimensional shape. Thereafter, a fine registration between the acquired second measurement image and the pre-acquired three-dimensional reference image is performed, based on the preliminary registration result.

After, performing a fine registration between the acquired second measurement image and the pre-acquired three-dimensional reference image, based on the result of the preliminary registration, contact the bone corresponding to the surgical area, with a verification tool, and check whether the verification tool is in contact with the bone on a virtual screen that is generated by the fine registration.

For one example, the surgical area of the patient may include an ear area, and the bone corresponding to the surgical area may include a bone that is located behind the patient's ear.

In another exemplary embodiment of the present invention, a registration method of images for surgery registration method of images for surgery includes acquiring a three-dimensional reference image of a surgical area of a patient before surgery, providing a grating-pattern light towards a bone corresponding to the surgical area, after an incision of the surgical area, acquiring a reflection image of the bone corresponding to the surgical area by the grating-pattern light, applying a bucket algorithm to the acquired first reflection image of the bone corresponding to the surgical area to measure a three-dimensional shape, and acquiring a measurement image from the three-dimensional shape, receiving a preliminary registration result between the acquired measurement image and the pre-acquired three-dimensional reference image from a worker, and performing a fine registration between the acquired measurement image and the pre-acquired three-dimensional reference image by using an iterative closest points (ICP) algorithm.

After performing a fine registration between the acquired second measurement image and the pre-acquired three-dimensional reference image, based on the result of the preliminary registration, contacting the bone corresponding to the surgical area with a verification tool, and checking whether the verification tool is in contact with the bone on a virtual screen that is generated by the fine registration.

In an exemplary embodiment, the surgical area of the patient may include an ear area, and the bone corresponding to the surgical area may include a bone that is located behind the patient's ear.

Advantageous Effects

According to the present invention, a three-dimensional reference image such as a computed tomography (CT) for a surgical area of a patient is previously acquired before surgery. Then, a three-dimensional shape of the surgical area is measured by applying a bucket algorithm using a pattern image according to a grating-pattern light, and thereafter a registration is performed between the measured image and the three-dimensional reference image. A preliminary registration may be performed by using a measurement image that is measured before cutting out the surgical area, and fine registration may be performed by using a measurement image that is measured after cutting out the surgical area. Alternatively, a measurement image that is measured after cutting out the surgical area may be used, and a preliminary registration and a fine registration may be performed by manually receiving registration result from a worker, and by using an ICP algorithm, respectively.

Therefore, two steps such as a preliminary registration and a fine registration are performed by using a measurement image and a reference image, to thereby acquire an accurate registration result.

In addition, a measurement image is acquired by applying a bucket algorithm that uses a pattern image according to a grating-pattern light, and may be quickly performed without any further preparation process in a surgery room, thereby saving cost in comparison with other methods that requires additional preparation, and reducing registration time.

In addition, when a separate verification process is performed, a more accurate registration result may be acquired.

EMBODIMENTS OF THE INVENTION

The invention is described more fully hereinafter with reference to the accompanying drawings, in which exemplary embodiments of the invention are shown.

However, this invention may be embodied in many different forms and should not be construed as limited to the embodiments set forth herein Numerical terms such as "one", "two", etc. may be used as cardinal numbers to indicate various structural elements, however, the structural elements should not be limited by the terms. The terms are only used to distinguish one structural element from another structural element. For example, a first structural element may be named as second structural element if the right is not beyond the scope, the same applies to the second structural element that may be named as the first structural element.

The terms used in the present application are only to explain the specific embodiment and is not intended to limit the present invention. The terms "a", "an" and "the" mean "one or more" unless expressly specified otherwise. The terms "including", "comprising", etc., are to designate features, numbers, steps, processes, structural elements, parts, and combined component of the application, and should be understood that it does not exclude one or more different features, numbers, steps, processes, structural elements, parts, combined component.

If not defined differently, all the terms used herein including technical or scientific terms, may be understood same as a person skilled in the art may understand.

The terms that are used herein are same as the terms defined in a commonly-used dictionary may be understood as same a contextual meaning, if not mentioned clearly, may not be understood as excessively or ideally.

The invention is described more fully hereinafter with reference to the accompanying drawings, in which exemplary embodiments of the invention are shown.

Figure 1:
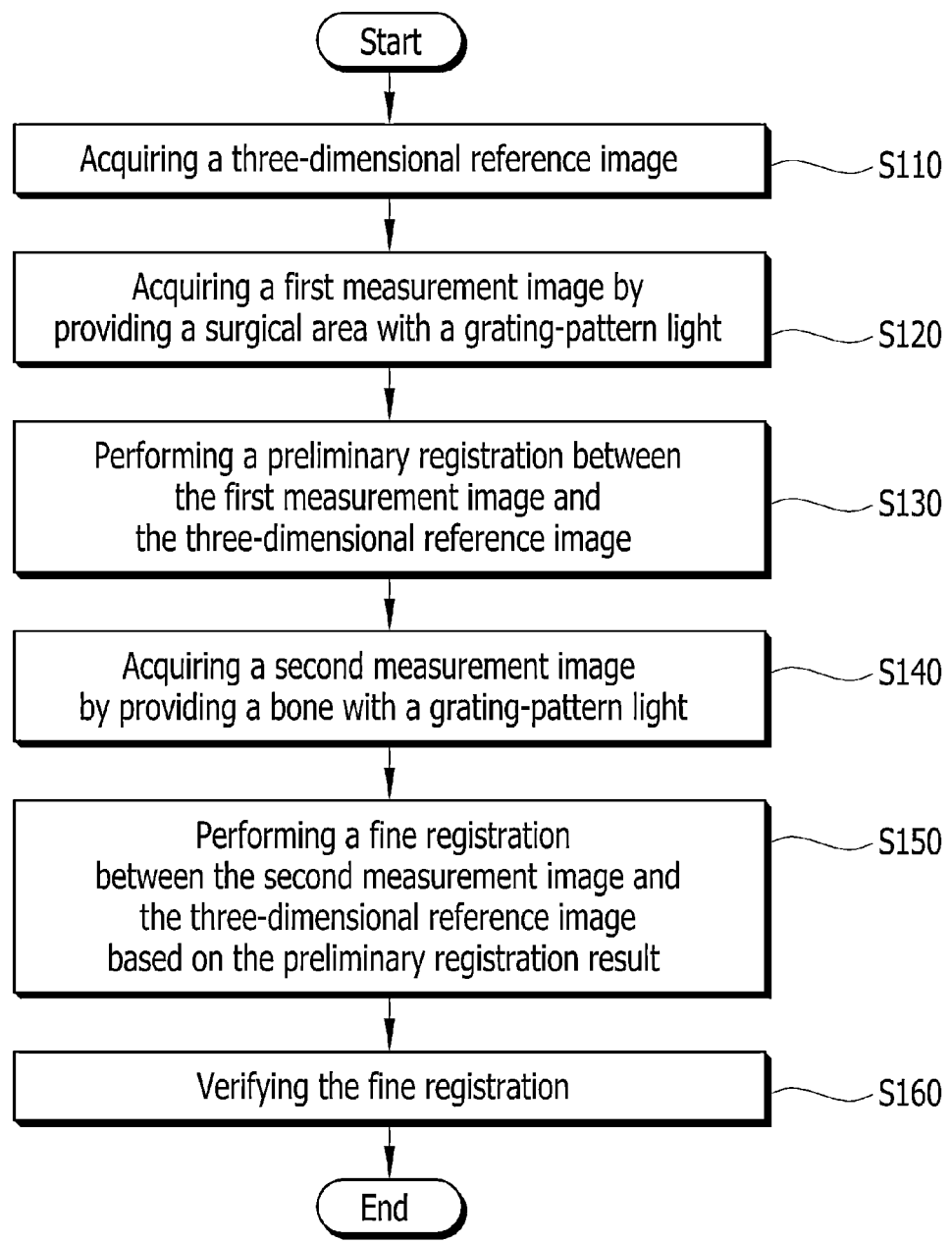
FIG. 1 is a flow chart showing a registration method of images for surgery according to an exemplary embodiment of the present invention.

FIG. 1 is a flow chart showing a registration method of images for surgery according to an exemplary embodiment of the present invention.

Referring to FIG. 1, in order to perform a registration of a surgery image according to an exemplary embodiment of the present invention, a three-dimensional reference image is acquired before surgery in step of S100.

Particularly, a three-dimensional reference image of a surgical area, for example, an ear area, of a patient is acquired before a surgery. The three-dimensional reference image may include a computed tomography (CT) image that is generally acquired in hospitals for diagnosis and treatment. Alternatively, the three-dimensional reference image may include a different three-dimensional image such as a magnetic resonance imaging (MRI).

Thereafter, the surgical area is provided with a grating-pattern light to acquire a first measurement image in step of S120.

Particularly, the surgical area is provided with a grating-pattern light, then after acquiring a first reflection image of the surgical area by the grating-pattern light, a bucket algorithm is applied to the acquired first reflection image of the surgical area to measure a three-dimensional shape, and a first measurement image is acquired from the three-dimensional image.

Figure 2:
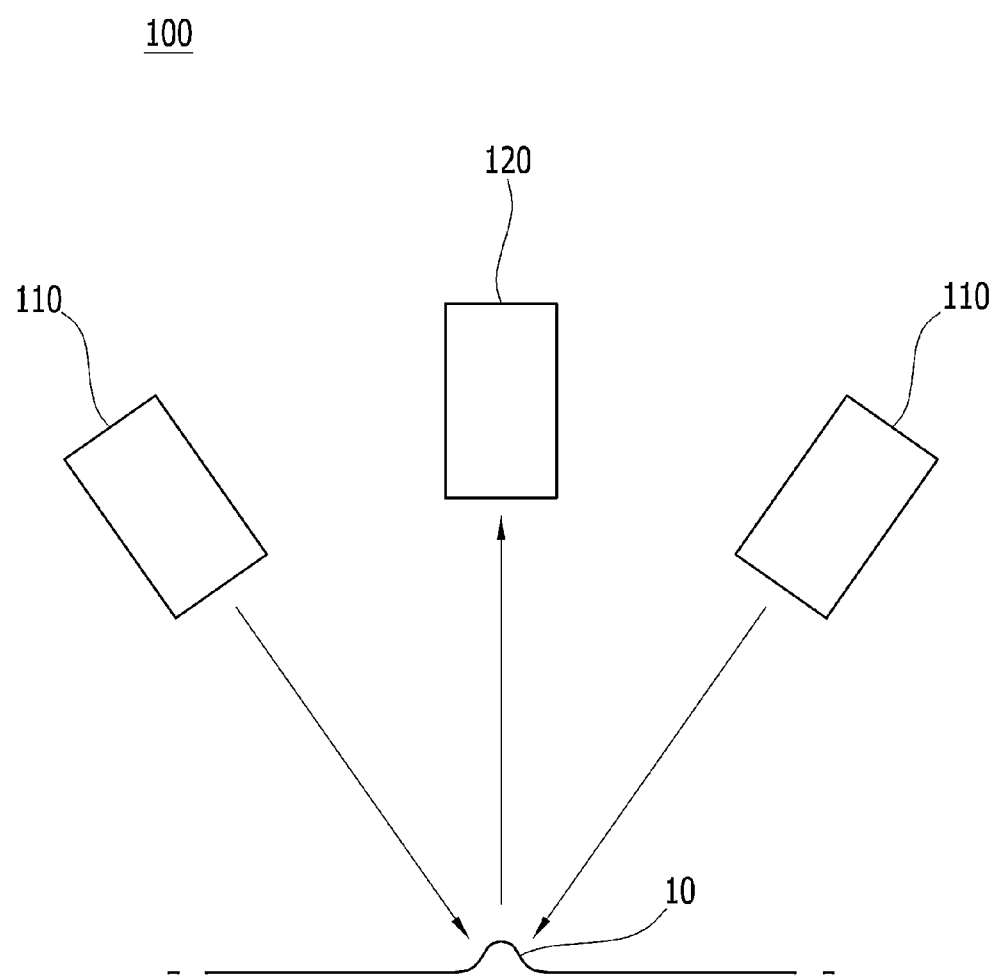
FIG. 2 is a conceptual view illustrating a process of acquiring a measurement image of a surgery area of a patient in FIG. 1.

FIG. 2 is a conceptual view illustrating a process of acquiring a measurement image of a surgery area of a patient in FIG. 1.

Referring to FIG. 2, a three-dimensional shape measurement apparatus 100 that provides grating pattern light to acquire a first measurement image may include a projection part 110, an image-capturing part 120, and a central control part (not shown).

The projection part 110 may be disposed to be inclined to the surgical area 10, and provides a grating-pattern light towards the surgical area 10. In an exemplary embodiment, the projection part 110 may include a light source unit, a grating unit, a grating-transfer unit, and a condensing lens, to provide a grating-pattern light. The light source unit generates light. The grating unit changes the light that is generated from the light source into the grating-pattern light having a grating-pattern. The grating transfer unit is connected with the grating unit to transfer the grating unit, for example, at least one of piezoelectric (PZT) transfer unit or fine-straight-line transfer unit. The condensing lens is disposed in a lower part of the grating unit to condense the grating-pattern light that passes the grating unit to the surgical area 10.

In an exemplary embodiment, the projection part 110 may provide N grating grating-pattern lights towards the surgical part 10 when the grating transfer unit sequentially moves the grating unit by N times, and the image-capturing part 120 that will be described later may image-capture N pattern images by sequentially receiving the N grating-pattern lights that are reflected from the surgical area 10. The N is a natural number, and may be, for example, 3 or 4.

The projection part 110 may employ an analog pattern scanning device that uses such as a PZT transfer unit as described above, and alternatively, employ a digital pattern scanning device that uses a digital micro mirror device (DMD).

The projection parts 110 may be plural. In this case, a grating-pattern light that is provided to the surgical area 10 may be provided in various directions to acquire various kinds of pattern images, so an error that may occur due to a shadow area that is generated dark by the shape of the surgical area 10 or a saturation area that shines brightly, may be prevented. For example, when three projection parts 110 are disposed in a equilateral triangle shape around the image-capturing part 120, three grating-pattern lights may be provided to the surgical area 10 from different directions, and when four projection parts 110 are disposed in a square-shape around the image-capturing part 120, four grating-pattern lights may be provided to the surgical area 10 from different directions.

Alternatively, the projection part 110 may be singular. In this case, since a grating-pattern light may be provided to the surgical area 10 from a single direction, an error that may partially occur due to a shadow area or a saturation area. However, such an error as is enough to deteriorate a registration, which will be described later, may not occur.

The image-capturing part 120 is disposed in an upper part of the surgical area 10, and receives a light that is reflected from the surgical area 10 to image-capture an image of the surgical area 10. In other words, the image-capturing part receives a light that is reflected from the surgical light that is provided from the projection part 110, to image-capture a plane image of the surgical area 10.

In an exemplary embodiment, the image-capturing part 120 may include a camera, an imaging lens, and a filter. The camera receives a light that is reflected from the surgical area 10 to image-capture a plane image of the surgical area, and may employ, for example, at least one of a CCD camera or a CMOS camera. The imaging lens is disposed in a lower part of the camera, and images a light that is reflected from the surgical area 10 at the camera. The filter is disposed in a lower part of the imaging lens to filter a light that is reflected from the surgical area 10 and provide the filtered light to the imaging lens, and may employ, for example, at least one of a frequency filter, a color filter, or a light intensity control filter.

The central control unit is connected with the projection part 110 and the image-capturing part 120, to control the action of the projection part 110 and the image-capturing part 120, and measures and outputs a three-dimensional shape of the surgical area 10 by using a pattern image that is image-captured by the image-capturing part 120.

Meanwhile, although not shown in the drawing, the three-dimensional shape measurement apparatus 100 may further include a jig part to fix the component.

Furthermore, in order to detect an accurate focus, in case that the three-dimensional shape measurement apparatus 100 may employ an analogue pattern scanning device, a laser spot may be adjusted to be at the central point of the camera by using an offset-axis laser, and in case that the three-dimensional shape measurement apparatus 100 may employ a digital pattern scanning device, the spot may be adjusted to be at the central point of the camera by the projection part 110 directly scanning the spot.

Referring again to FIG. 1, in a next step, a preliminary registration between a first measurement image and a three-dimensional reference image is performed in step of S130.

Particularly, a first registration is performed between the first measurement image that is acquired in step of S120 which is acquired by providing the surgical area 10 with a grating-pattern light and the three-dimensional reference image that is acquired before surgery in step of S110. The first registration is a registration prior to a fine registration that will be described later, and corresponds to a coarse matching.

Figure 3:
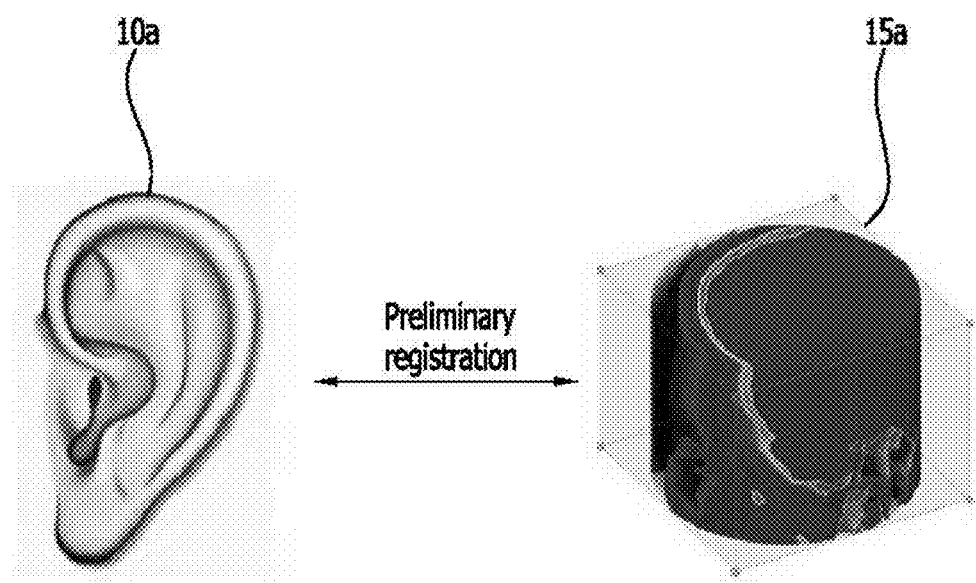
FIG. 3 is a conceptual view illustrating a process of preliminary registration in FIG. 1.

FIG. 3 is a conceptual view illustrating a process of preliminary registration in FIG. 1.

Referring to FIG. 3, when the surgical area 10 is, for example, an ear area, a preliminary registration is performed between a first measurement image 10a of the ear area, which is acquired by providing the ear area with a grating-pattern light, and a three-dimensional reference image 15a of the ear area, which is acquired before surgery.

Referring again to FIG. 1, a second measurement image is acquired by providing a bone with a grating-pattern light in step of S140.

Particularly, after cutting out the surgical area 10 for surgery, a bone corresponding to the surgical area 10 is provided with a grating-pattern light, then a second reflection image according to the bone corresponding to the surgical area 10 is acquired, thereafter a three-dimensional shape is measured by applying a bucket algorithm to the acquired second reflection image of the bone corresponding to the surgical area, and then a second measurement image is acquired from the three-dimensional shape.

Since the step of acquiring the second measurement image is substantially the same as the step of acquiring the first measurement image as described in FIG. 2, except that a measurement target is a bone corresponding to the surgical area 10, any further description will be omitted.

Referring again to FIG. 1, a fine registration is performed between the second measurement image and the three-dimensional reference image, based on the result of the preliminary registration in step of S150.

Particularly, a secondary registration is performed between the second measurement image that is acquired by providing a grating-pattern light to a bone corresponding to the surgical area 10 in step of S140 and the three-dimensional reference image that is acquired before the surgery in step of S110. The secondary registration corresponds to a fine registration.

Figure 4:
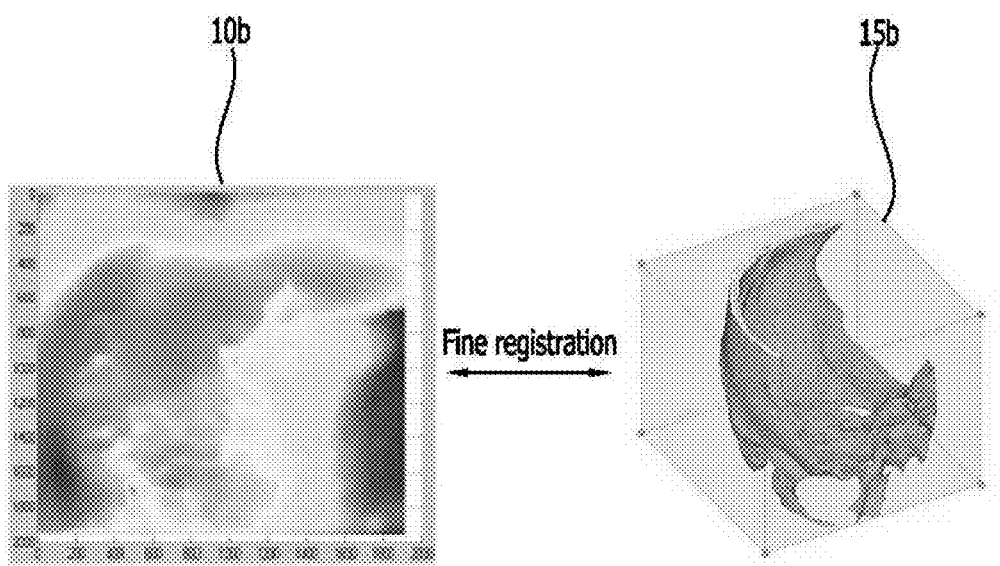
FIG. 4 is a conceptual view illustrating a process of fine registration in FIG. 1.

FIG. 4 is a conceptual view illustrating a process of fine registration in FIG. 1.

Referring to FIG. 4, when the surgical area 10 is, for example, an ear area, a fine registration is performed between the second measurement image 10b of the bone corresponding to the ear area, which is acquired by providing the ear area with a grating-pattern light after cutting out the ear area, and a three-dimensional reference image 15b of the bone corresponding to the ear area, which is a CT image acquired before surgery.

Referring again to FIG. 1, a registration result according to the fine registration may be selectively verified in step of S160.

Particularly, after contacting a bone corresponding to the surgical area with a verification tool, a virtual screen that is generated by the fine registration may check whether the verification tool is in contact with the bone. When the virtual screen shows that the verification tool is properly contacted, the registration may be determined as valid.

Figure 5:
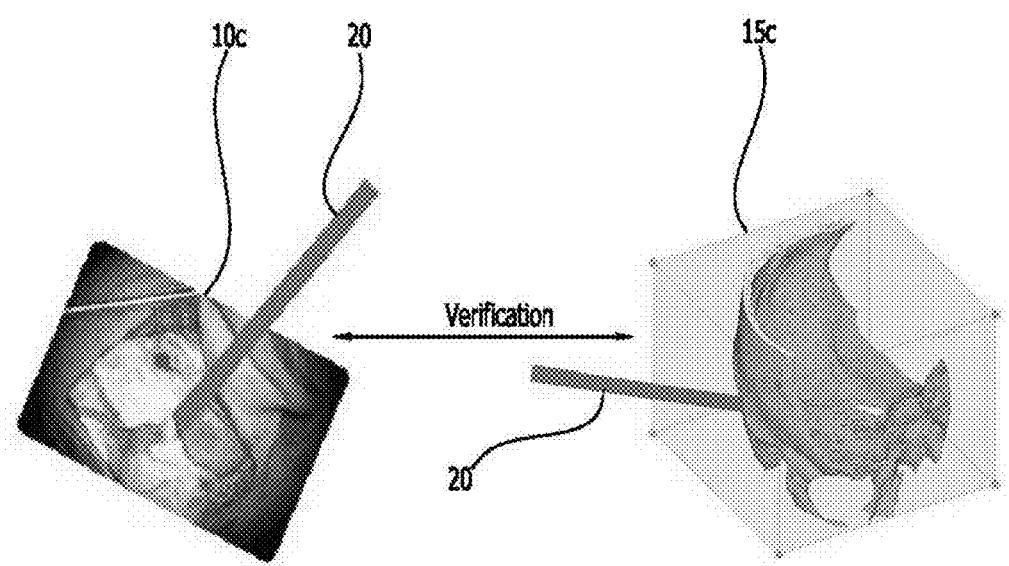
FIG. 5 is a conceptual view illustrating a process of verifying a fine registration in FIG. 1.

FIG. 5 is a conceptual view illustrating a process of verifying a fine registration in FIG. 1.

Referring to FIG. 5, when the surgical area 10 is, for example, an ear area, after contacting the bone corresponding to the ear area with a verification tool 20 (10c), it is verified whether the verification tool 20 is properly in contact on the three-dimensional reference image of the ear area, which is a CT image acquired before surgery (15c).

Figure 6:
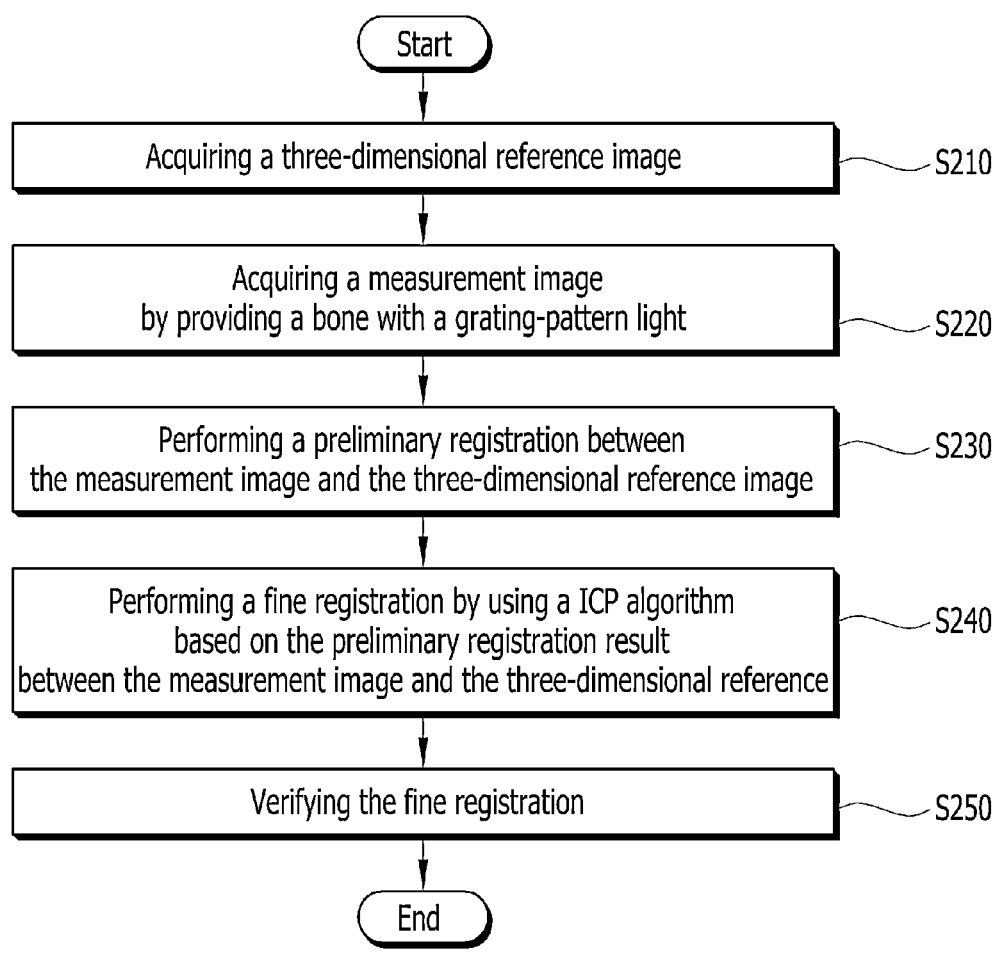
FIG. 6 is a flow chart showing a registration method of images for surgery according to another exemplary embodiment of the present invention.

FIG. 6 is a flow chart showing a registration method of images for surgery according to another exemplary embodiment of the present invention.

Referring to FIG. 6, in order to perform a registration of images for surgery according to another exemplary embodiment of the present invention, first, a three-dimensional reference image is acquired before surgery in step of S210.

Since the present step is substantially the same as the step of acquiring the three-dimensional reference image described in step of S110, any further description will be omitted.

Then, a bone is provided with a grating-pattern light, to acquire a measurement image in step of S220.

Since the present step is substantially the same as the step of acquiring the second measurement image described in step of S140, any further description will be omitted.

Then, a preliminary registration is performed between the measurement image and the three-dimensional reference image in step of S230.

Particularly, a first registration is performed between the measurement image that is acquired in step of acquiring a measurement image by providing a bone with a grating-pattern light in step of S220 and the three-dimensional reference image that is acquired in step of acquiring a three-dimensional reference image in step of S210, and the registration result is received from a worker. The first registration corresponds to a coarse matching.

Figure 7:
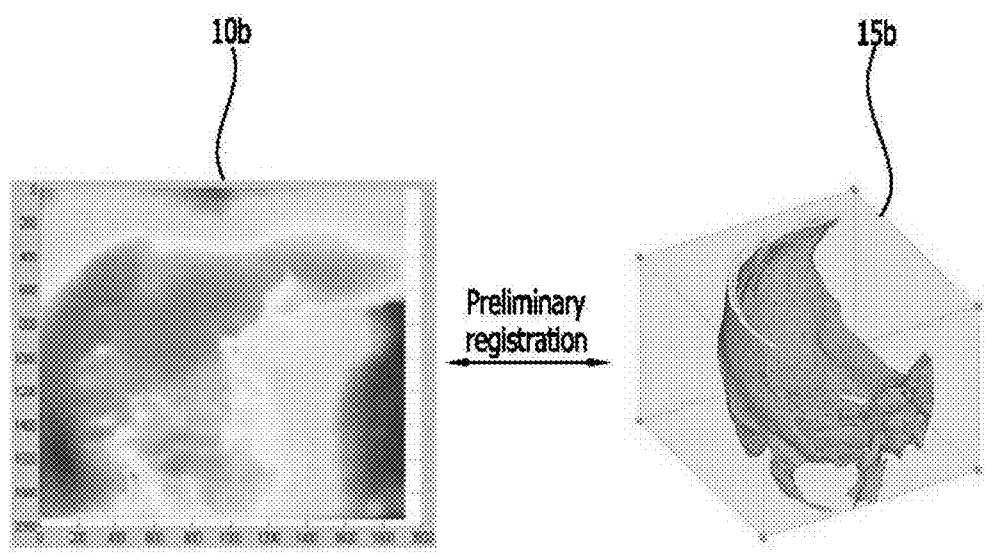
FIG. 7 is a conceptual view illustrating a process of preliminary registration in FIG. 6.

FIG. 7 is a conceptual view illustrating a process of preliminary registration in FIG. 6.

Referring to FIG. 7, when the surgical area 10 is, for example, an ear area, a preliminary registration is performed between a measurement image 10b of the bone corresponding to the ear area, which is acquired by providing the ear area with a grating-pattern light after cutting out the ear area and a three-dimensional reference image 15b of the bone corresponding to the ear area, which is a CT image acquired before surgery, and the registration is received from a worker.

Referring again to FIG. 6, a fine registration is performed between the measurement image and the three-dimensional reference image based on the result of the preliminary registration by using an iterative closest points algorithm (ICP) in step of S240.

Since, the ICP algorithm is a widely known algorithm for three-dimensional image registration and is used in various fields, detailed description will be omitted.

Then, selectively, a registration result according to the fine registration may be verified in step of S250.

Since the present step is substantially the same as the step of verifying a registration result according to the fine registration described in step of S160, any further description will be omitted.

According to the present invention, a three-dimensional reference image such as a computed tomography (CT) for a surgical area of a patient is previously acquired before surgery. Then, a three-dimensional shape of the surgical area is measured by applying a bucket algorithm using a pattern image according to a grating-pattern light, and thereafter a registration is performed between the measured image and the three-dimensional reference image. A preliminary registration may be performed by using a measurement image that is measured before cutting out the surgical area, and fine registration may be performed by using a measurement image that is measured after cutting out the surgical area. Alternatively, a measurement image that is measured after cutting out the surgical area may be used, and a preliminary registration and a fine registration may be performed by manually receiving registration result from a worker, and by using an ICP algorithm, respectively.

Therefore, two steps such as a preliminary registration and a fine registration are performed by using a measurement image and a reference image, to thereby acquire an accurate registration result.

In addition, a measurement image is acquired by applying a bucket algorithm that uses a pattern image according to a grating-pattern light, and may be quickly performed without any further preparation process in a surgery room, thereby saving cost in comparison with other methods that requires additional preparation, and reducing registration time.

In addition, when a separate verification process is performed, a more accurate registration result may be acquired.

The detailed description of the present invention is described with regard to the preferable embodiment of the present invention, however, a person skilled in the art may amend or modify the present invention within the spirit or scope in the following claim of the present invention. Therefore, the detailed description described above and the drawing illustrated hereinafter does not limit the technical idea of the invention.

What is claimed is:

1. A registration method of images for surgery, the method comprising:
   acquiring, by an image-acquiring apparatus, a three-dimensional reference image of a surgical area of a patient before surgery;
   providing, by a shape measurement apparatus, a grating-pattern light towards the surgical area;
   acquiring, by the shape measurement apparatus, a first reflection image of the surgical area by the grating-pattern light;
   measuring, by the shape measurement apparatus, a first three-dimensional shape by using the acquired first reflection image of the surgical area, and acquiring a first measurement image from the first three-dimensional shape;
   performing, by a processing unit, a preliminary registration between the acquired first measurement image and the three-dimensional reference image;
   providing, by the shape measurement apparatus, the grating-pattern light towards a bone corresponding to the surgical area, after an incision of the surgical area;
   acquiring, by the Shape measurement apparatus, a second reflection image of the bone corresponding to the surgical area by the grating-pattern light;
   measuring, by the shape measurement apparatus, a second three-dimensional shape by using the acquired second reflection image of the bone corresponding to the surgical area, and acquiring a second measurement image from the second three-dimensional shape;
   performing, by the processing unit, a fine registration between the acquired second measurement image and the three-dimensional reference image, based on a result of the preliminary registration.

2. The method of claim 1, wherein after the performing the fine registration between the acquired second measurement image and the three-dimensional reference image, based on the result of the preliminary registration, further comprising:
   contacting the bone corresponding to the surgical area, with a verification tool; and
   checking whether the verification tool is in contact with the bone on a virtual screen that is generated by the fine registration.

3. The method of claim 1, wherein the surgical area of the patient includes an ear area, and the bone corresponding to the surgical area includes a bone that is located behind the patient's ear.

4. A registration method of images for surgery, the method comprising:
   acquiring, by an image-acquiring apparatus, a three-dimensional reference image of a surgical area of a patient before surgery;
   providing, by a shape measurement apparatus, a grating-pattern light towards a bone corresponding to the surgical area, after an incision of the surgical area;
   acquiring, by the shape measurement apparatus, a reflection image of the bone corresponding to the surgical area by the grating-pattern light;

measuring, by the shape measurement apparatus, a three-dimensional shape by using the acquired first reflection image of the bone corresponding to the surgical area, and acquiring a measurement image from the three-dimensional shape;

receiving, by a processing unit, a preliminary registration result between the acquired measurement image and the three-dimensional reference image from a worker; and performing, by the processing unit, a fine registration between the measurement image and the three-dimensional reference image.

5. The method of claim 4, wherein after performing the fine registration between the acquired measurement image and the three-dimensional reference image, further comprising:

contacting the bone corresponding to the surgical area, with a verification tool; and checking whether the verification tool is in contact with the bone on a virtual screen that is generated by the fine registration.

6. The method of claim 4, wherein the surgical area of the patient includes an ear area, and the bone corresponding to the surgical area includes a bone that is located behind the patient's ear.

\* \* \* \* \*